United States Patent [19]

Semler et al.

[11] Patent Number: 5,557,005
[45] Date of Patent: Sep. 17, 1996

[54] PROCESS FOR PREPARING 3-CHLOROANTHRANILIC ALKYL ESTERS OF HIGH PURITY FROM 3-CHLOROANTHRANILIC ACID

[75] Inventors: Günther Semler, Kelkheim; Michael Meier, Frankfurt, both of Germany

[73] Assignee: Hoechst Aktiengesellschaft, Germany

[21] Appl. No.: 449,251

[22] Filed: May 24, 1995

Related U.S. Application Data

[63] Continuation of Ser. No. 230,897, Apr. 21, 1994, abandoned.

[30] Foreign Application Priority Data

Apr. 22, 1993 [DE] Germany .............................. 43 13 174.3

[51] Int. Cl.$^6$ .................................................. C07C 229/56
[52] U.S. Cl. ............................................................ 560/47
[58] Field of Search ..................................................... 560/47

[56] References Cited

U.S. PATENT DOCUMENTS

| 4,261,996 | 4/1981 | Sircar et al. | 424/251 |
|---|---|---|---|
| 4,306,074 | 12/1981 | Tonne et al. | 560/47 |
| 4,316,020 | 2/1982 | Reissenweber | 544/105 |
| 4,486,221 | 12/1984 | Seybold et al. | 71/90 |
| 5,068,392 | 11/1991 | McKendry et al. | 560/46 |
| 5,118,832 | 6/1992 | Pearson | 560/47 |

FOREIGN PATENT DOCUMENTS

| 0020969 | 1/1981 | European Pat. Off. . |
| 2925175 | 1/1981 | Germany . |
| 3106111 | 9/1982 | Germany . |
| 1549297 | 8/1979 | United Kingdom . |

OTHER PUBLICATIONS

Deutsche Chemische Gesellschaft Chemische Berichte, Bd. 32, 1898 pp. 2159–2172.

*Primary Examiner*—Gary Geist
*Assistant Examiner*—Barbara S. Frazier
*Attorney, Agent, or Firm*—Connolly & Hutz

[57] ABSTRACT

Process for preparing 3-chloroanthranilic alkyl esters by reacting 3-chloroanthranilic acid, in an inert solvent, with from 0.8 to 5 parts by weight of phosgene, and reacting the 3-chloroisatoic anhydride which is formed with an alkanol, where appropriate in the presence of an esterification catalyst, to give the 3-chloroanthranilic alkyl ester.

20 Claims, No Drawings

PROCESS FOR PREPARING 3-CHLOROANTHRANILIC ALKYL ESTERS OF HIGH PURITY FROM 3-CHLOROANTHRANILIC ACID

This application is a continuation of Ser. No. 08/230,897, filed Apr. 21, 1994, now abandoned.

The invention relates to a process for preparing 3-chloroanthranilic alkyl esters of high purity by reacting 3-chloroanthranilic acid with phosgene in an inert organic solvent and esterifying the 3-chloroisatoic anhydride thus formed with an alkanol.

3-Chloroanthranilic alkyl esters are important intermediates for preparing pharmaceutical and agricultural products (see, e.g.: DE 2,812,586 and DE 3,142,727).

Pure 3-chloroanthranilic alkyl esters have previously been prepared only in a 5-step synthesis starting from anthranilic esters (U.S. Pat. No. 5,068,392). According to U.S. Pat. No. 5,068,392, (pure) 3-chloroanthranilic alkyl esters can be prepared starting from anthranilic esters by means of a 5-step synthesis. The amino group of the anthranilic alkyl ester is first acetylated, bromination then takes place in the para position to the acetylated amino group, and this is then followed by chlorination in the ortho position to the acetylated amino group. Subsequently, the bromine is removed by reduction and the acetamino group is de-acetylated. The process is fairly elaborate and is found to be problematical owing to the use of bromine chloride or elemental bromine and chlorine. In addition to this, a series of unwanted waste products is inevitably formed. Apart from this, the preparation of 3-chloroanthranilic alkyl esters has only been described in the form of a mixture together with chloroanthranilic alkyl esters substituted in the 5 or 6 positions. Thus, according to EP 20 969, 3-chlorophthalic anhydride is reacted with ammonia, alkali metal hydroxide and alkali metal hypochlorite, and the resulting mixture of 5-chloroisatoic and 8-chloroisatoic anhydrides is esterified with alkanols to give a mixture of 3-chloroanthranilic and 6-chloroanthranilic alkyl esters. 5-Chloroanthranilic and 3,5-dichloroanthranilic alkyl esters arise as by-products in the amounts of from 23 to 48% and from 2 to 6%, respectively, when 3-chloroanthranilic alkyl esters are prepared in accordance with U.S. Pat. No. 5,118,832 by the reaction of anthranilic esters with 1,3-dichloro-5,5-dimethylhydantoin. After complicated removal of the by-products, methyl 3-chloroanthranilate is obtained in 49.6% yield.

There is, therefore, a need for a simple process, which can easily be carried out on an industrial scale, for preparing 3-chloroanthranilic alkyl esters which does not suffer from the abovementioned disadvantages and makes 3-chloroanthranilic alkyl esters available not only at high purity but also in high yield.

This object is achieved by a process for preparing 3-chloroanthranilic alkyl esters. In this process, 3-chloroanthranilic acid (1) is reacted, in an inert organic solvent, with from 0.8 to 5 parts by weight of phosgene, and the 3-chloroisatoic anhydride (2) which is formed is reacted with an alkanol, where appropriate in the presence of an esterification catalyst, to give the 3-chloroanthranilic alkyl ester (3).

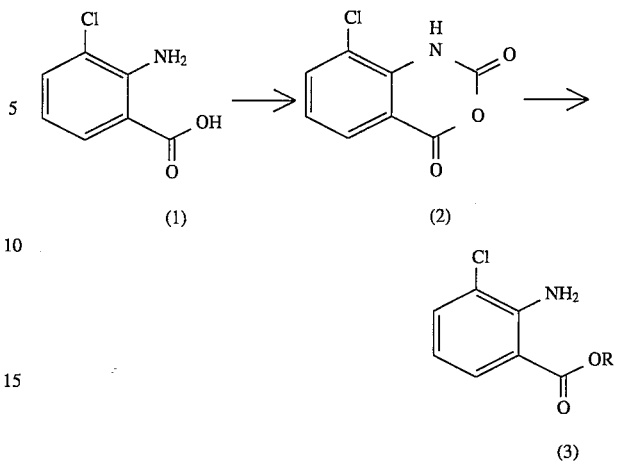

In the process according to the invention, an aromatic hydrocarbon, a chlorinated aromatic hydrocarbon, or mixtures thereof, is/are employed as the inert organic solvent. In many cases, it has proved efficacious to use toluene, a xylene, a mixture of xylene isomers, chlorobenzene, dichlorobenzene and/or a chlorotoluene in about 4 to 20, preferably is 8 to 12, parts by weight for each part by weight of 3-chloroanthranilic acid. When pure 3-chloroanthranilic acid is used, the mother liquor from the phosgenation step can be employed in place of the pure solvent. Naturally, larger quantities of solvent may also be used, although this diminishes the advantage gained in space and time.

It has been found to be advantageous to employ from 0.8 to 5, in particular from 1.6 to 3.1, parts by weight of phosgene in the reaction for each part by weight of 3-chloroanthranilic acid.

In many cases, it has proved efficacious to treat 3-chloroanthranilic acid, in a first step at temperatures of from 5° to 50° C., in particular of from 15° to 35° C., with from 0.5 to 3, in particular from 1 to 2, parts by weight of phosgene for each part by weight of 3-chloroanthranilic acid, and subsequently, in a second step, to heat the mixture to temperatures of from 80 to 140, in particular of from 90° to 120° C., and to treat it with an additional 0.3 to 2, in particular 0.6 to 1.1, parts by weight of phosgene for each part by weight of 3-chloroanthranilic acid, then carefully to separate off any phosgene which is still present, and to isolate it by filtering the 3-chloroisatoic anhydride thus prepared.

However, it is also possible to carry out the reaction of 3-chloroanthranilic acid with phosgene in a single step. In this case, it is advisable to employ temperatures of from 80 to 120 in particular of from 90° to 110° C., and to add the phosgene approximately to the extent that it is being consumed by the reaction. Care must be taken to ensure thorough mixing. The quantity of phosgene to be used is the same as the requirement which was indicated for the two-step procedure. The reaction may be allowed to proceed under elevated pressure, if this is necessary to keep down the length of the reaction. After the reaction has finished, any remaining phosgene must be carefully removed. The 3-chloroisatoic anhydride which is formed is subsequently separated off by filtration.

Alkanols having 1 to 4 carbon atoms may expediently be employed for the subsequent reaction (esterification) of the 3-chloroisatoic anhydride.

Alkanols which give good results in this reaction are methanol, ethanol, n-propanol, isopropanol, butanol, isobutanol, sec.-butanol and tert.-butanol, in particular methanol.

It has additionally been found useful to carry out the esterification using from 1 to 20, in particular from 2 to 10, parts by weight of alkanol to 1 part by weight of 5-chloroisatoic anhydride.

In addition, it has proved efficacious to carry out the esterification at from 5° to 90° C., in particular at from 15° to 75° C. Depending on the catalysts, losses in yield can occur at higher temperatures and when the reaction times are too long.

The compounds described in the literature (see, e.g., EP 20 969) can be used as esterification catalysts. Basic compounds, such as the hydroxides, alcoholates, carbonates and/or hydrogen carbonates of the alkali metals, in particular the corresponding compounds of sodium and/or potassium, are suitable.

The catalyst is customarily employed at from 0.01 to 0.8, in particular from 0.1 to 0.5, of an equivalent for each equivalent of 3-chloroisatoic anhydride.

An additional advantage of the process according to the invention is that 3-chloroanthranilic acid of technical quality (purity about 90%) can also be employed, while still permitting the isolation of 3-chloroanthranilic alkyl ester of high purity. For example, a 3-chloroanthranilic acid which is obtained by the process in EP 0,528,375 is a suitable starting material. 3-Chloroanthranilic alkyl esters are formed by the above-described process in approximately 90% yield, based on 3-chloroanthranilic acid. The purity is >99%.

The examples below serve to illustrate the process according to the invention without limiting it.

EXAMPLE 1

Preparation of 3-chloroisatoic anhydride 190.7 g of 90% 3-chloroanthranilic acid, corresponding to 171.6 g (1.0 mol) of 100% 3-chloroanthranilic acid, are initially introduced, in 1,970.0 g of chlorobenzene, into a four-necked flask having a stirrer, a thermometer and a reflux condenser cooled down to −20° C., and 300.0 g of phosgene are then metered in at room temperature over a period of about 3 h while stirring thoroughly. The reaction mixture is heated to 100° C. and a further 150.0 g of phosgene are passed in over a period of 2 h. After that, the mixture is stirred at 100° C. for a further 1 h, and the phosgene is subsequently removed at this temperature using nitrogen. After cooling to about 25° C., the crystals which have precipitated out are filtered off with suction, and the filter cake is washed with 2×50 ml of chlorobenzene and dried at 100° C. in vacuo. 190.0 g of 3-chloroisatoic anhydride, having a purity by GC of >99%, are obtained, corresponding to 96.2% of theory. In that which follows, m.p. stands for melting point, s.p. for solidification point and MS for mass spectrum.

m.p.: 223° C.

MS: 197 ($M^+$), 153 ($M^+$—$CO_2$), 125

EXAMPLE 2

Preparation of 3-chloroisatoic anhydride 190.7 g of 90% 3-chloroanthranilic acid, corresponding to 171.6 g (1.0 mol) of 100% 3-chloroanthranilic acid, are initially introduced, in 1,820.0 g of toluene, into a four-necked flask having a stirrer, a thermometer and a reflux condenser cooled down to −20° C., and 300.0 g of phosgene are then metered in at room temperature over a period of about 3 h while stirring thoroughly. The reaction mixture is heated to 100° C. and a further 150.0 g of phosgene are passed in over a period of 2 h. After that, the mixture is stirred at 100° C. for a further 1 h, and subsequently blown free of phosgene at this temperature using nitrogen. After cooling to about 25° C., the crystals which have precipitated out are filtered off with suction, and the filter cake is washed with 2×50 ml of toluene and dried at 100° C. in vacuo. 188.3 g of 3-chloroisatoic anhydride, having a purity by GC of >99%, are obtained, corresponding to 95.2% of theory.

m.p.: 223° C.

MS: 197 ($M^{30}$), 153 ($M^+$—$CO_2$), 125

EXAMPLE 3

Preparation of 3-chloroisatoic anhydride (single-step)

171.6 g (1.0 mol) of 99.7% 3-chloroanthranilic acid are initially introduced, in 1,720.0 g of chlorobenzene, into a four-necked flask having a stirrer, a thermometer and a reflux condenser operated at −20° C., and 440.0 g of phosgene are gassed in at 100° C. over a period of about 3 h while stirring thoroughly. After that, the mixture is stirred at 100° C. for a further 1 h, and is subsequently blown free of phosgene at this temperature using nitrogen. After cooling to about 25° C., the crystals which have precipitated out are filtered off with suction and the filter cake is washed with 2×50 ml of chlorobenzene and dried at 100° C. in vacuo. 184.9 g of 3-chloroisatoic anhydride, having a purity by GC of >99%, are obtained, corresponding to 93.6% of theory.

m.p.: 223 ° C.

MS: 197 ($M^+$), 153 ($M^+$—$CO_2$), 125

EXAMPLE 4

Preparation of methyl 3-chloroanthranilate 98.8 g (0.5 mol) of 3-chloroisatoic anhydride and 25 g of sodium carbonate are stirred, at 25° C., into 200 g of methanol, and the mixture is stirred at this temperature for a further 3 h. Subsequently, it is filtered, washed with methanol and the methanol is distilled off under atmospheric pressure, and the methyl 3-chloroanthranilate is then distilled at 115° C./15 mbar. The yield amounts to 86.3 g, corresponding to 93.0% of theory. The purity by GC is >99.5%.

s.p.: 36.7° C.

MS: 185 ($M^{30}$), 153 ($M^+$—$CH_3OH$), 125

EXAMPLE 5

Preparation of methyl 3-chloroanthranilate 98.8 g (0.5 mol ) of 3-chloroisatoic anhydride and 9.0 g of potassium carbonate are stirred, at 25° C., into 250 g of methanol, and the mixture is stirred at this temperature for a further 3 h. Subsequently, it is filtered, washed with methanol and the methanol is distilled off under atmospheric pressure, and 87.7 q of methyl 3-chloroanthranilate are distilled at 115° C./15 mbar. This corresponds to a yield of 94.5% of theory. The purity by GC is >99.5%.

s.p.: 37.5° C. MS: 185 ($M^{30}$), 153 ($M^{30}$—$CH_3OH$), 125

EXAMPLE 6

Preparation of methyl 3-chloroanthranilate 98.8 g (0.5 mol) of 3-chloroisatoic anhydride are stirred into 200 g of methanol, 10 g of sodium methoxide, as a 30% solution in methanol, are added at 25° C., and the mixture is heated to 68° C. and stirring then continued at this temperature for a further 2 h. Subsequently, it is filtered, washed with methanol and the methanol is distilled off under atmospheric pressure, and 84.8 g of methyl 3-chloroanthranilate are distilled at 115° C./15 mbar. This corresponds to a yield of 91.4% of theory. The purity by GC is >99.5%.

s.p.: 37.0° C.

MS: 185 ($M^{30}$), 153 ($M^+$—$CH_3OH$), 125

We claim:

1. A process for preparing a 3-chloroanthranilic alkyl ester, comprising the following steps:
   a. reacting 3-chloroanthranilic acid, in an inert solvent, with from 0.8 to 5 parts by weight of phosgene per part by weight of 3-chloroanthranilic acid, wherein said inert solvent comprises an aromatic hydrocarbon, a chlorinated aromatic hydrocarbon, or mixtures thereof
   b. reacting the resulting 3-chloroisatoic anhydride intermediate with an alkanol, optionally in the presence of an esterification catalyst, wherein said esterification catalyst is hydroxide, alcoholate, carbonate or hydrogen carbonate of the alkali metals, to obtain the 3-chloroanthranilic alkyl ester.

2. The process as claimed in claim 1, wherein said aromatic hydrocarbon or chlorinated aromatic hydrocarbon comprises toluene, a xylene, a mixture of xylene isomers, chlorobenzene, dichlorobenzene or a chlorotoluene.

3. The process as claimed in claim 1, wherein, in said step (a), the reaction medium comprises from 4 to 20 parts by weight of inert solvent for each part by weight of 3-chloroanthranilic acid.

4. The process as claimed in claim 1, wherein 1.6 to 3.1 parts by weight of phosgene are reacted with each part by weight of 3-chloroanthranilic acid.

5. The process as claimed in claim 1, wherein the phosgene is reacted portionwise with the 3-chloroanthranilic acid, the first portion of phosgene ranging from 0.5 to 3 parts by weight of phosgene for each part by weight of 3-chloroanthranilic acid.

6. The process as claimed in claim 5, wherein said first portion ranges from 1 to 2 parts by weight of phosgene for each part by weight of 3-chloroanthranilic acid.

7. The process as claimed in claim 1, wherein the phosgene is reacted portionwise with the 3-chloroanthranilic acid, the first portion of phosgene being reacted at from 5° to 50° C.

8. The process as claimed in claim 7, wherein 3-chloroanthranilic acid is reacted with said first portion of phosgene at from 15° to 35° C.

9. The process as claimed in claim 1, wherein the phosgene is reacted in a plurality of portions, including a first portion and a second portion, the second portion ranging from 0.3 to 2 parts by weight of phosgene for each part by weight of 3-chloroanthranilic acid.

10. The process as claimed in claim 9, wherein said second portion ranges from 0.6 to 1.1 parts by weight of phosgene for each part by weight of 3-chloroanthranilic acid.

11. The process as claimed in claim 9, wherein the reaction mixture is heated to a temperature ranging from 80° to 140° C. for the reaction of said second portion of phosgene.

12. The process as claimed in claim 9, wherein the reaction mixture is heated to a temperature ranging from 90° to 120° C. for the reaction of said second portion of phosgene.

13. The process as claimed in claim 1, wherein said step (a) is carried out with introduction of phosgene approximately to the extent that the phosgene is being consumed by the reaction, at from 80° to 120° C.

14. The process as claimed in claim 1, wherein said alkanol has 1 to 4 carbon atoms.

15. The process as claimed in claim 1, wherein from 1 to 20 parts by weight of alkanol are reacted with each part by weight of 3-chloroisatoic anhydride.

16. The process as claimed in claim 1, wherein the 3-chloroisatoic anhydride is reacted with the alkanol at from 5° to 90° C.

17. The process as claimed in claim 1, wherein the 3-chloroisatoic anhydride is reacted with the alkanol at from 15° to 75° C.

18. The process as claimed in claim 1, wherein said step (b) is carried out in the presence of said esterification catalyst.

19. The process as claimed in claim 18, wherein the amount of esterification catalyst present is from 0.01 to 0.8 equivalent for each equivalent of 3-chloroisatoic anhydride, and the 3-chloroanthranilic alkyl ester is isolated from the esterification medium.

20. The process as claimed in claim 1, wherein said esterification catalyst is present in an amount from 0.1 to 0.5 of an equivalent for each equivalent of the 3-chloroisatoic anhydride and the purity of the 3-chloroanthranilic alkyl ester is greater than 99%.

* * * * *